United States Patent
Sekine et al.

(10) Patent No.: US 12,070,740 B2
(45) Date of Patent: Aug. 27, 2024

(54) CATALYST STRUCTURE AND METHOD FOR PRODUCING SAME, AND METHOD FOR PRODUCING HYDROCARBON BY USE OF CATALYST STRUCTURE

(71) Applicant: FURUKAWA ELECTRIC CO., LTD., Tokyo (JP)

(72) Inventors: Kaori Sekine, Tokyo (JP); Yuichiro Banba, Tokyo (JP); Yukako Nakai, Tokyo (JP); Mai Nishii, Tokyo (JP); Masayuki Fukushima, Tokyo (JP); Sadahiro Kato, Tokyo (JP); Takao Masuda, Sapporo (JP); Yuta Nakasaka, Sapporo (JP); Takuya Yoshikawa, Sapporo (JP)

(73) Assignee: FURUKAWA ELECTRIC CO., LTD., Tokyo (JP)

(*) Notice: Subject to any disclaimer, the term of this patent is extended or adjusted under 35 U.S.C. 154(b) by 511 days.

(21) Appl. No.: 17/299,748

(22) PCT Filed: Dec. 3, 2019

(86) PCT No.: PCT/JP2019/047298
§ 371 (c)(1),
(2) Date: Jun. 3, 2021

(87) PCT Pub. No.: WO2020/116475
PCT Pub. Date: Jun. 11, 2020

(65) Prior Publication Data
US 2022/0016608 A1 Jan. 20, 2022

(30) Foreign Application Priority Data
Dec. 3, 2018 (JP) .................. 2018-226932

(51) Int. Cl.
*B01J 29/04* (2006.01)
*B01J 35/40* (2024.01)
(Continued)

(52) U.S. Cl.
CPC ............. *B01J 29/044* (2013.01); *B01J 35/40* (2024.01); *B01J 35/643* (2024.01); *B01J 37/02* (2013.01); *B01J 37/10* (2013.01); *B01J 37/16* (2013.01)

(58) Field of Classification Search
CPC ...... B01J 29/03; B01J 29/0356; B01J 29/044; B01J 29/44; B01J 29/46; B01J 29/24;
(Continued)

(56) References Cited

U.S. PATENT DOCUMENTS 4,499,209 A 2/1985 Hoek et al.
11,161,101 B2* 11/2021 Kato ................. B01J 23/464
(Continued)

FOREIGN PATENT DOCUMENTS

CN 102078818 A 6/2011
CN 103889577 A 6/2014
(Continued)

OTHER PUBLICATIONS

International Search Report issued on Mar. 10, 2020 in PCT/JP2019/047298 filed on Dec. 3, 2019 (2 pages).
(Continued)

*Primary Examiner* — Colin W. Slifka
(74) *Attorney, Agent, or Firm* — Oblon, McClelland, Maier & Neustadt, L.L.P.

(57) ABSTRACT

A catalyst structure that allows prevention of aggregation of fine particles of a functional substance, suppresses decrease of catalyst activity, and thus enables extension of the lifetime of the catalyst structure. A catalyst structure has a carrier that is formed from a zeolite-type compound and has a porous
(Continued)

structure. The functional substance includes a first element that is at least one metallic element selected from the group consisting of cobalt (Co), nickel (Ni), iron (Fe), and ruthenium (Ru), and at least one second element selected from the group consisting of metallic elements in group 1, group 2, group 4, group 7, and group 12 on the periodic table. The carrier has paths connected to each other. The functional substance is present in at least the paths of the carrier.

20 Claims, 4 Drawing Sheets

(51) Int. Cl.
*B01J 35/64* (2024.01)
*B01J 37/02* (2006.01)
*B01J 37/10* (2006.01)
*B01J 37/16* (2006.01)

(58) Field of Classification Search
CPC ...... B01J 29/072; B01J 29/085; B01J 29/185; B01J 29/087; B01J 29/088; B01J 29/143; B01J 29/146; B01J 29/605; B01J 29/63; B01J 29/40; B01J 29/405; B01J 29/48; B01J 29/65; B01J 29/655; B01J 29/68; B01J 29/69; B01J 29/74; B01J 29/76; B01J 29/7084; B01J 29/7088; B01J 29/7669; B01J 29/7676; B01J 29/7869; B01J 29/7876; B01J 29/7215; B01J 29/7057; B01J 29/7615; B01J 29/7815; B01J 2229/14; B01J 2229/18; B01J 2229/186; B01J 35/0073; B01J 35/109; B01J 37/02; B01J 37/10; B01J 37/16; B01J 37/08; C07C 1/04
USPC .................................. 502/60, 74, 77, 78, 79
See application file for complete search history.

(56) References Cited

U.S. PATENT DOCUMENTS

| | | | |
|---|---|---|---|
| 11,547,987 B2 * | 1/2023 | Masuda | .............. B01J 29/0358 |
| 11,654,422 B2 * | 5/2023 | Masuda | .............. B01J 37/0211 |
| | | | 502/64 |
| 2003/0139283 A1 | 7/2003 | Herbst et al. | |
| 2008/0280754 A1 | 11/2008 | Toledo Antonio et al. | |
| 2008/0293990 A1 | 11/2008 | Stevenson et al. | |
| 2016/0137516 A1 | 5/2016 | Kegnaes et al. | |
| 2016/0296913 A1 | 10/2016 | Takahama et al. | |

FOREIGN PATENT DOCUMENTS

| | | |
|---|---|---|
| CN | 105358251 A | 2/2016 |
| CN | 106457229 A | 2/2017 |
| CN | 110730687 A | 1/2020 |
| EP | 0 455 307 A1 | 11/1991 |
| EP | 1 331 032 A2 | 7/2003 |
| EP | 3 016 741 | 5/2016 |
| JP | 59-102440 A | 6/1984 |
| JP | 4-227847 A | 8/1992 |
| JP | 2000-070720 A | 3/2000 |
| JP | 2009-505830 A | 2/2009 |
| JP | 2010-527769 A | 8/2010 |
| JP | 2016-529190 A | 9/2016 |
| JP | 2017-128480 A | 7/2017 |
| WO | WO 2008/153758 A2 | 12/2008 |
| WO | WO 2010/097108 A1 | 9/2010 |
| WO | WO 2010/097224 A2 | 9/2010 |
| WO | WO 2013/057319 A2 | 4/2013 |
| WO | WO 2015/001123 A1 | 1/2015 |
| WO | WO 2015/072573 A1 | 5/2015 |
| WO | WO 2017/072698 A1 | 5/2017 |

OTHER PUBLICATIONS

Combined Chinese Office Action and Search Report issued Feb. 8, 2023 in Patent Application No. 201980078000.4 (with English machine translation), 32 pages.
Notification of Reasons for Refusal issued Mar. 7, 2023 in Japanese Patent Application No. 2020-559942 (with English machine translation), 12 pages.
Extended European Search Report issued Aug. 3, 2022 in European Patent Application No. 19892836.8, 8 pages.
Combined Chinese Office Action and Search Report issued on Oct. 28, 2023 in Chinese Patent Application No. 201980078000.4 (with English translation), 31 pages.
Zhong Bangke, "Catalysis of Fine Chemical Processes", Sinopec Press, Aug. 31, 2002, pp. 34-35 (4 total pages).
U.S. Appl. No. 17/299,609, filed Jun. 3, 2021, US 2022/0016607A1, Mai Nishii.
U.S. Appl. No. 17/299,718, filed Jun. 3, 2021, US 2022/0048014A1, Mai Nishii.
U.S. Appl. No. 17/299,641, filed Feb. 10, 2022, US 2022/0161239A1, Yuichiro Banba.
U.S. Appl. No. 17/167,280, filed Feb. 4, 2021, US 2021/0162387A1, Sadahiro Kato.
U.S. Appl. No. 17/930,056, filed Sep. 6, 2022, US 2023/0009052A1, Takao Masuda.
U.S. Appl. No. 18/171,140, filed Feb. 17, 2023, US 2023/0201814A1, Takao Masuda.
U.S. Pat. No. 11,161,101, Nov. 2, 2021, US 2019/0039056A1, Sadahiro Kato.
U.S. Pat. No. 11,684,909, Jun. 27, 2023, US 2020/0114335A1, Takao Masuda.
U.S. Pat. No. 11,680,211, Jun. 20, 2023, US 2020/0115640A1, Takao Masuda.
U.S. Pat. No. 11,654,422, May 23, 2023, US 2020/0094229A1, Takao Masuda.
U.S. Pat. No. 11,666,894, Jun. 6, 2023, US 2020/0114338A1, Takao Masuda.
U.S. Pat. No. 11,547,987, Jan. 10, 2023, US 2020/0114339A1, Takao Masuda.
U.S. Pat. No. 11,655,157, May 23, 2023, US 2020/0115248A1, Takao Masuda.
U.S. Pat. No. 11,648,538, May 16, 2023, US 2020/0108374A1, Takao Masuda.
U.S. Pat. No. 11,648,542, May 16, 2023, US 2020/0114341A1, Takao Masuda.
U.S. Appl. No. 16/698,496, filed Nov. 27, 2019, US 2020/0094232A1, Takao Masuda.
U.S. Appl. No. 17/299,639, filed Feb. 10, 2022, US 2022/0161242A1, Yuichiro Banba.
U.S. Appl. No. 17/299,646, filed Jun. 3, 2021, US 2022/0023848A1, Yukako Nakai.
U.S. Appl. No. 17/299,672, filed Jun. 3, 2021, US 2022/0032276A1, Mai Nishii.
U.S. Appl. No. 18/000,459, filed Dec. 1, 2022, US 2023/0211325A1, Yuichiro Banba.
U.S. Appl. No. 16/698,567, filed Nov. 27, 2019, US 2020/0114336A1, Takao Masuda.
U.S. Pat. No. 11,648,543, May 16, 2023, US 2020/0108378A1, Takao Masuda.
U.S. Appl. No. 16/698,545, filed Nov. 27, 2019, US 2020/0114337A1, Takao Masuda.
Jun. 3, 2021, US 2022/0016608A1, Kaori Sekine.

* cited by examiner

CATALYST STRUCTURE AND METHOD FOR PRODUCING SAME, AND METHOD FOR PRODUCING HYDROCARBON BY USE OF CATALYST STRUCTURE

TECHNICAL FIELD

The present invention relates to a catalyst structure, a method of producing the catalyst structure, and a method of producing hydrocarbons using the catalyst structure.

BACKGROUND ART

Examples of known techniques utilizing catalytic reactions include methods of producing hydrocarbon compounds for use as raw materials for liquid fuel products, such as synthetic oils as alternative fuels to petroleum, and synthetic fuels. A known example of the catalytic reaction is the Fischer-Tropsch synthesis reaction (hereinafter, also referred to as "FT synthesis reaction") by which hydrocarbons, specifically, liquid hydrocarbons are produced from a syngas composed mainly of carbon monoxide gas (CO) and hydrogen gas ($H_2$). Examples of the catalyst for use in the FT synthesis reaction include a catalyst disclosed in Patent Document 1, which includes a support, such as silica or alumina, and an active metal, such as cobalt or iron, on the support; and a catalyst disclosed in Patent Document 2, which includes cobalt, zirconium, or titanium, and silica.

The catalyst for use in the FT synthesis reaction can be obtained in the form of a supported cobalt or ruthenium oxide (unreduced catalyst) by, for example, impregnating a support, such as silica or alumina, with a cobalt or ruthenium salt and then firing the impregnated support. The catalyst obtained in such a way should be made sufficiently active for the FT synthesis reaction. As disclosed in Patent Document 3, therefore, the obtained catalyst should be reduced by being brought into contact with a reducing gas, such as a hydrogen gas, so that the oxide of cobalt and/or ruthenium is converted into an active metal form.

As disclosed in Patent Document 4, it is known that the FT synthesis reaction is accompanied by an extremely large amount of heat generation, which causes a hot spot at a locally overheated portion of the catalyst surface, so that the catalytic activity may decrease as side reactions (such as carbonaceous substance precipitation) occur on the catalyst surface due to the hot spot. To prevent the formation of such a hot spot, it is necessary to prevent aggregation of fine particles (metal fine particles) of an active metal species, which is a functional material for acting as a catalyst, and to provide dispersed active sites. In order to prevent aggregation of metal fine particles, a support capable of strongly interacting with the active metal species may be used to prevent the metal fine particles from easily aggregating together.

A known example of such a method includes a sol-gel method by which metal fine particles are highly dispersed and supported. In such a sol-gel method, the active metal species can be uniformly introduced at the atomic level at the stage of synthesizing a metal oxide for serving as a support. In such a supported metal catalyst, the active metal species are extremely highly dispersed and incorporated in the lattices of the metal oxide support and thus do not easily aggregate during different processes and reactions. Unfortunately, such a catalyst has problems, such as insufficient catalytic activity resulting from difficulty in activation of the catalyst prior to the reaction, which is due to the strong bonding between the active metal species and the support; and difficulty in uniformly making nanosized particles due to difficulty in controlling the particle size.

The aggregation of metal fine particles also causes a decrease in the effective surface area of the catalyst, which leads to a decrease in the catalytic activity and thus makes the life of the catalyst shorter than usual. This requires the catalyst to be replaced or refreshed at short intervals, which raises problems such as complicated replacement operation and failure of resource-saving.

In the technology disclosed in Patent Documents 3 and 4, $H_2O$ produced during the FT synthesis reaction may oxidize the active metal in the catalyst to reduce the catalytic activity for the FT synthesis reaction. Therefore, a need exists to prevent a decrease in the activity of the catalyst subjected to the FT synthesis reaction.

Such prevention of the decrease in catalytic activity is also required for catalysts for use in other chemical reactions as well as for catalysts for use in the FT synthesis reaction. For example, Patent Documents 5 and 6 disclose a technique for preventing catalyst aggregation, which includes preparing amorphous silica-coated metal fine particles using an emulsion technique; and hydrothermally treating the fine particles to incorporate the metal fine particles into zeolite crystals. The emulsion technique used to obtain the amorphous silica-coated metal fine particles includes mixing a surfactant and a metal source in an organic solvent to form an emulsion; adding a reducing agent to the emulsion to form metal fine particles; and then adding a silane coupling agent to the emulsion to form a silica layer on the surfaces of the metal fine particles. Unfortunately, when metal fine particles are produced using such an emulsion technique, the size of the resulting metal fine particles is affected by the size of the droplets formed during the emulsion forming process and by the tendency of the metal particles to aggregate. In general, base metals are vulnerable to aggregation and can hardly remain in a nanoparticle size. According to Patent Documents 5 and 6, particles of only the noble metal Rh, Au, or Pt are observed to be nanosized. Patent Documents 5 and 6 are silent on whether fine particles of Ru, a base metal, vulnerable to aggregation, or oxides thereof can be nanosized when they are incorporated in zeolite. In the emulsion technique, the organic solvent and surfactant used during the formation of a zeolite structure can remain as impurities, which can easily have an adverse effect on the thermal stability of zeolite.

Patent Document 1: Japanese Unexamined Patent Application, Publication No. H04-227847

Patent Document 2: Japanese Unexamined Patent Application, Publication No. S59-102440

Patent Document 3: PCT International Publication No. WO2015/072573

Patent Document 4: Japanese Unexamined Patent Application, Publication No. 2000-70720

Patent Document 5: Japanese Unexamined Patent Application, Publication No. 2017-128480

Patent Document 6: PCT International Publication No. WO2010/097108

DISCLOSURE OF THE INVENTION

Problems to be Solved by the Invention

It is an object of the present invention to provide a catalyst structure in which functional material fine particles are prevented from aggregating and which has a long life resulting from prevention of a decrease in catalytic activity, to provide a method of producing such a catalyst structure, and to provide a method of producing hydrocarbons using such a catalyst structure.

Means for Solving the Problems

As a result of intensive studies for achieving the object, the inventors have found a catalyst structure including: a support that has a porous structure and includes a zeolite-type compound; and a functional material present in the support, wherein the functional material includes at least one first element selected from the group consisting of cobalt (Co), nickel (Ni), iron (Fe), and ruthenium (Ru); and at least one second element selected from the group consisting of metal elements belonging to Groups 1, 2, 4, 7, and 12 of the periodic table, the support has channels communicating with one another, and the functional material is present at least in the channels of the support, and have completed the present invention with respect to the findings that fine particles of the functional material are prevented from aggregating in such a catalyst structure and such a catalyst structure can resist a decrease in catalytic activity and have a long life.

Specifically, the present invention has the following principal features.

(1) A catalyst structure including:
- a support that has a porous structure and includes a zeolite-type compound; and
- at least one functional material present in the support,
- at least one functional material including:
- at least one first metal element selected from the group consisting of cobalt (Co), nickel (Ni), iron (Fe), and ruthenium (Ru); and
- at least one second metal element selected from the group consisting of metal elements belonging to Groups 1, 2, 4, 7, and 12 of the periodic table, wherein
- the support has channels communicating with one another, and the functional material is present at least in the channels of the support.

(2) The catalyst structure according to aspect (1), wherein the second element is at least one metal element selected from the group consisting of potassium (K), magnesium (Mg), titanium (Ti), zirconium (Zr), manganese (Mn), and zinc (Zn).

(3) The catalyst structure according to aspect (1) or (2), wherein a mass ratio of a content of the second element to a content of the first element is from 0.01 to 2.00.

(4) The catalyst structure according to any one of aspects (1) to (3), wherein a total content of the first element is 0.5% by mass or more with respect to the mass of the catalyst structure.

(5) The catalyst structure according to any one of aspects (1) to (4), wherein a total content of the second element is 5% by mass or less with respect to the mass of the catalyst structure.

(6) The catalyst structure according to any one of aspects (1) to (5), wherein a content of the second element is lower than a content of the first element.

(7) The catalyst structure according to any one of aspects (1) to (6), wherein the functional material is in the form of metal oxide fine particles including one or both of an oxide of the first element and an oxide of the second element.

(8) The catalyst structure according to any one of aspects (1) to (6), wherein the functional material is in the form of metal fine particles including one or both of the first element and the second element.

(9) The catalyst structure according to aspect (8), wherein the metal fine particles include one or both of: fine particles of an alloy including the first element and the second element; and at least two types of single metal fine particles including fine particles of the first element and fine particles of the second element.

(10) The catalyst structure according to any one of aspects (1) to (9), wherein the channels have any one of a one-dimensional pore, a two-dimensional pore, and a three-dimensional pore of a framework structure of the zeolite-type compound; and an enlarged pore portion different from all of the one-, two-, and three-dimensional pores, and the functional material is present at least in the enlarged pore portion.

(11) The catalyst structure according to aspect (10), wherein the enlarged pore portion connects a plurality of pores constituting one of the one-, two-, and three-dimensional pores.

(12) The catalyst structure according to any one of aspects (1) to (11), wherein the functional material has an average particle size larger than the average inner diameter of the channels.

(13) The catalyst structure according to any one of aspects (10) to (12), wherein the functional material has an average particle size equal to or smaller than the inner diameter of the enlarged pore portion.

(14) The catalyst structure according to any one of aspects (1) to (13), wherein the functional material has an average particle size of 0.08 nm to 30 nm.

(15) The catalyst structure according to any one of aspects (1) to (14), wherein a ratio of the average particle size of the functional material to the average inner diameter of the channels is from 0.05 to 300.

(16) The catalyst structure according to any one of aspects (1) to (15), wherein the channels have an average inner diameter of 0.1 nm to 1.5 nm.

(17) The catalyst structure according to any one of aspects (10) to (16), wherein the enlarged pore portion has an inner diameter of 0.5 nm to 50 nm.

(18) The catalyst structure according to any one of aspects (1) to (17), further including at least one additional functional material held on an outer surface of the support.

(19) The catalyst structure according to aspect (18), wherein the additional functional material includes one or more metals selected from the group consisting of cobalt (Co), nickel (Ni), iron (Fe), and ruthenium (Ru), or an alloy thereof.

(20) The catalyst structure according to aspect (18) or (19), wherein the additional functional material includes one or more metals selected from the group consisting of elements belonging to Groups 1, 2, 4, 7, and 12 of the periodic table, or an alloy thereof.

(21) The catalyst structure according to any one of aspects (18) to (20), wherein the content of the additional functional material present in the support is higher than the content of the additional functional material held on the outer surface of the support.

(22) A hydrocarbon production system including the catalyst structure according to any one of aspects (1) to (21).

(23) A method of producing a catalyst structure, the method including:
- a firing step that includes firing a precursor material (B) including a metal-containing solution and a precursor material (A) for forming a support having a porous structure and including a zeolite-type compound, the precursor material (A) being impregnated with the metal-containing solution; and a hydrothermal treatment step that includes hydrothermally treating a precursor material (C) obtained by firing the precursor material (B), wherein
the metal-containing solution is a solution containing:
at least one first metal element selected from the group consisting of cobalt (Co), nickel (Ni), iron (Fe), and ruthenium (Ru); and
at least one second metal element selected from the group consisting of metal elements belonging to Groups 1, 2, 4, 7, and 12 of the periodic table.

(24) The method of producing a catalyst structure according to aspect (23), further including a step that includes reducing the precursor material (C) having undergone the hydrothermal treatment.

(25) The method of producing a catalyst structure according to aspect (23) or (24), wherein the firing step is preceded by adding the metal-containing solution in multiple portions to the precursor material (A) to impregnate the precursor material (A) with the metal-containing solution.

(26) The method of producing a catalyst structure according to any one of aspects (23) to (25), wherein the firing step is preceded by adjusting the amount of addition of the metal-containing solution to the precursor material (A) so as to adjust the ratio of the number of silicon (Si) atoms in the precursor material (A) to the number of first element ($M_1$) atoms in the metal-containing solution (Si/$M_1$ atomic ratio) to 10 to 1,000.

(27) The method of producing a catalyst structure according to any one of aspects (23) to (26), wherein the firing step is preceded by adjusting the amount of addition of the metal-containing solution to the precursor material (A) so as to adjust the ratio of the number of silicon (Si) atoms in the precursor material (A) to the number of second element ($M_2$) atoms in the metal-containing solution (Si/$M_2$ atomic ratio) to 1,000 to 10,000.

(28) A method of producing a catalyst structure, the method including:
a firing step that includes firing a precursor material (B) including a first metal-containing solution and a precursor material (A) for forming a support having a porous structure and including a zeolite-type compound, the precursor material (A) being impregnated with the first metal-containing solution;
a hydrothermal treatment step that includes hydrothermally treating a precursor material (C) obtained by firing the precursor material (B); and
a step that includes firing a precursor material (D) impregnated with a second metal-containing solution, the precursor material (D) being a product obtained by hydrothermally treating the precursor material (C), wherein the first metal-containing solution is a solution containing at least one first metal element selected from the group consisting of cobalt (Co), nickel (Ni), iron (Fe), and ruthenium (Ru), and
the second metal-containing solution is a solution containing at least one second metal element selected from the group consisting of metal elements belonging to Groups 1, 2, 4, 7, and 12 of the periodic table.

(29) The method of producing a catalyst structure according to aspect (28), further including a step that includes reducing the precursor material (D) having been fired.

(30) The method of producing a catalyst structure according to any one of aspects (23) to (29), wherein the firing step is preceded by adding a nonionic surfactant in an amount of 50 to 500% by mass to the precursor material (A).

(31) The method of producing a catalyst structure according to any one of aspects (23) to (30), wherein the hydrothermal treatment step further includes mixing a structure-directing agent with the precursor material (C).

(32) The method of producing a catalyst structure according to any one of aspects (23) to (31), wherein the hydrothermal treatment step is performed in a basic atmosphere.

(33) A method of producing a hydrocarbon, the method including synthesizing a hydrocarbon from carbon monoxide and hydrogen using a catalyst including
a catalyst structure including:
a support that has a porous structure and includes a zeolite-type compound; and
at least one functional material present in the support, the functional material including:
at least one first metal element selected from the group consisting of cobalt (Co), nickel (Ni), iron (Fe), and ruthenium (Ru); and
at least one second metal element selected from the group consisting of metal elements belonging to Groups 1, 2, 4, 7, and 12 of the periodic table, wherein
the support has channels communicating with one another, and the functional material is present at least in the channels of the support.

Effects of the Invention

The present invention makes it possible to provide a catalyst structure in which functional material fine particles are prevented from aggregating and which has a long life resulting from prevention of a decrease in catalytic activity, to provide a method of producing such a catalyst structure, and to provide a method of producing hydrocarbons using such a catalyst structure.

BRIEF DESCRIPTION OF THE DRAWINGS

FIGS. 1A and 1B are views schematically showing the inner structure of a catalyst structure according to an embodiment of the present invention, in which FIG. 1A is a perspective view (shown partially in cross-sectional view), and FIG. 1B is a partially enlarged cross-sectional view;

FIGS. 2A and 2B are partially enlarged cross-sectional views for illustrating an example of the function of the catalyst structure of FIGS. 1A and 1B, in which FIG. 2A is a view for illustrating a sieving function, and FIG. 2B is a view for illustrating a catalytic ability;

PREFERRED MODE FOR CARRYING OUT THE INVENTION

Figure 1A:
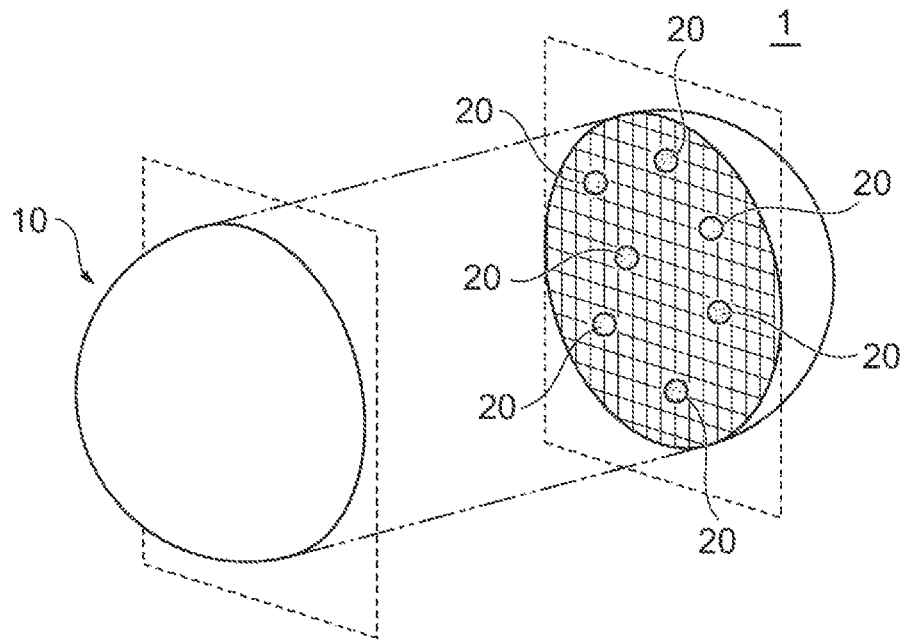
Figure 1B:
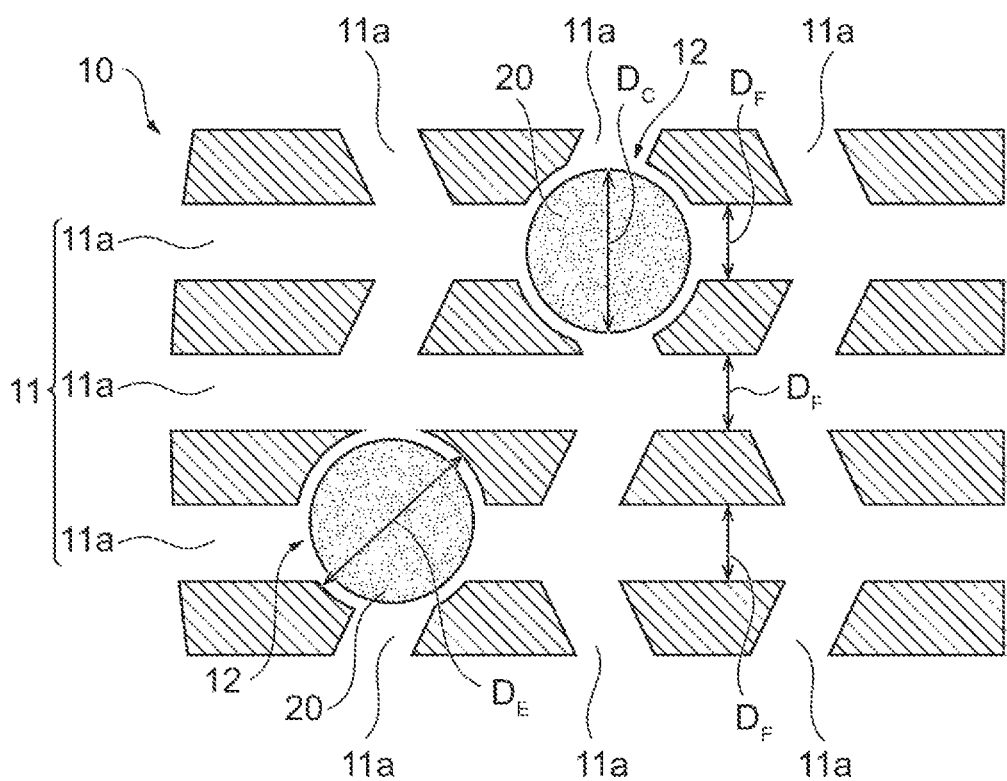

Hereinafter, embodiments of the present invention will be described in detail regarding the drawings.
Features of Catalyst Structure
FIGS. 1A and 1B are views schematically showing the features of a catalyst structure according to an embodiment of the present invention, in which FIG. 1A is a perspective view (shown partially in cross-sectional view), and FIG. 1B is a partially enlarged cross-sectional view. It should be noted that FIGS. 1A and 1B show only an example of the catalyst structure and the features shown in FIGS. 1A and 1B, such as shapes and dimensions, are not intended to limit those of the present invention.

As shown in FIG. 1A, a catalyst structure 1 includes a support 10 having a porous structure and including a zeolite-type compound; and at least one functional material 20 present in the support 10 and including first and second elements described later.

In the catalyst structure 1, multiple pieces of functional material 20 are enclosed in the porous structure of the support 10. A piece of the functional material 20 is a catalytic material that has a catalytic ability (catalytic activity) at least when used as a catalyst, and is in the form of a fine particle. The functional material will be described in detail later.

As shown in FIG. 1B, the support 10 has a porous structure and has channels 11 communicating with one another. The support 10 preferably has multiple pores 11*a*, which form the channels 11. The functional material 20 is present at least in channels 11 of the support 10 and is preferably held at least in channels 11 of the support 10.

Such a feature restricts the movement of the functional material 20 in the support 10 and effectively prevents aggregation of fine particles of the functional material 20. This results in effective prevention of a decrease in the effective surface area of the functional material 20 and results in long-term retention of the catalytic activity of the functional material 20. In other words, the features of the catalyst structure 1 make it possible to prevent a decrease in catalytic activity, which would otherwise be caused by aggregation of fine particles of the functional material 20, and to prolong the life of the catalyst structure 1. Moreover, thanks to the prolonged life of the catalyst structure 1, the frequency of replacement of the catalyst structure 1 can be reduced, and the amount of discarding of the used catalyst structure 1 can be greatly reduced, which leads to resource-saving.

In general, when used in a fluid (e.g., heavy oil, a reforming gas such as $NO_x$), a catalyst structure may receive an external force from the fluid. In such a case, if a functional material is only deposited on the outer surface of a support 10, there will be a problem in that, due to the influence of the external force from the fluid, the functional material can easily separate from the outer surface of the support 10. On the other hand, in the catalyst structure 1, the functional material 20 is present at least in channels 11 of the support 10 and thus less likely to separate from the support 10 even when receiving the influence of an external force from a fluid. Specifically, when the catalyst structure 1 is placed in a fluid, the fluid flowing into the channels 11 through the pores 11*a* of the support 10 encounters flow channel resistance (frictional force), so that the velocity of the fluid flowing in the channels 11 would be lower than that of the fluid flowing on the outer surface of the support 10. Due to the influence of such flow channel resistance, the pressure applied from the fluid onto the functional material 20 held in the channels 11 becomes lower than that applied outside the support 10. Therefore, the functional material 20 is effectively prevented from separating from the support 10, and the catalytic activity of the functional material 20 can be stably maintained for a long period of time. The flow channel resistance would be higher when the channel 11 of the support 10 has multiple curves or branches and the interior of the support 10 has a more complicated three-dimensional structure.

The channels 11 preferably have any one of a one-dimensional pore, a two-dimensional pore, and a three-dimensional pore, which are defined by the framework structure of the zeolite-type compound, and preferably have an enlarged pore portion 12 different from all of the one-, two-, and three-dimensional pores. In this case, the functional material 20 is preferably present at least in the enlarged pore portion 12 and more preferably enclosed at least in the enlarged pore portion 12. The enlarged pore portion 12 also preferably connects multiple pores 11*a* to one another when the pores 11*a* form any of the one-, two-, and three-dimensional pores. According to this feature, another channel different from the one-, two-, or three-dimensional pore is present in the support 10 to exert the function of the functional material 20 more effectively. As used herein, the term "one-dimensional pore" or "one-dimensional pores" refers to a tunnel- or cage-shaped pore constitutes a one-dimensional channel or refers to multiple tunnel- or cage-shaped pores constituting multiple one-dimensional channels. The term "two-dimensional pore" refers to a channel having multiple one-dimensional channels connected two-dimensionally. The term "three-dimensional pore" refers to a channel having multiple one-dimensional channels connected three-dimensionally. According to this feature, the movement of the functional material 20 is further restricted in the support 10, and separation of the functional material 20 and aggregation of fine particles of the functional material 20 are more effectively prevented. The term "enclosed" indicates that the functional material 20 is included in the support 10. In this regard, the functional material 20 and the support 10 do not always have to be in direct contact with each other, and the functional material 20 may be indirectly held by the support 10 with an additional material (e.g., a surfactant) provided between the functional material 20 and the support 10.

FIG. 1B shows a case in which the functional material 20 is enclosed in the enlarged pore portion 12. Such a feature is non-limiting, and alternatively, the functional material 20 may be held in the channel 11 while partially protruding out of the enlarged pore portion 12. Alternatively, the functional material 20 may be partially embedded in a portion of the channel 11 other than the enlarged pore portion 12 (e.g., an inner wall portion of the channel 11) or may be held by fixation or the like.

The channel 11 preferably has a three-dimensional structure including a branching or junction portion inside the support 10, and the enlarged pore portion 12 is preferably provided at the branching or junction portion of the channel 11.

The average inner diameter $D_F$ of the channels 11 provided in the support 10 may be calculated from the average of the short and long diameters of the pores 11*a*, which form any of the one-, two-, and three-dimensional pores. The average inner diameter $D_F$ of the channels 11 is typically 0.1 nm to 1.5 nm and preferably 0.5 nm to 0.8 nm. The inner diameter $D_E$ of the enlarged pore portion 12 is typically 0.5 nm to 50 nm, preferably 1.1 nm to 40 nm, and more preferably 1.1 nm to 3.3 nm. The inner diameter $D_E$ of the enlarged pore portion 12 depends, for example, on the pore size of the precursor material (A) described later and the particle diameter of the functional material 20 to be enclosed in the enlarged pore portion 12. The inner diameter $D_E$ of the enlarged pore portion 12 is such that it is possible to enclose the functional material 20.

The support 10 includes a zeolite-type compound. Examples of the zeolite-type compound include silicate compounds, such as zeolite (aluminosilicate), cation-exchanged zeolite, and silicalite; zeolite analogue compounds, such as aluminoborates, aluminoarsenates, and germanates; and phosphate-based zeolite analogue materials, such as molybdenum phosphate. Among them, the zeolite-type compound is preferably a silicate compound.

The framework structure of the zeolite-type compound may be selected from FAU type (Y or X type), MTW type, MFI type (ZSM-5), FER type (ferrierite), LTA type (A type), MWW type (MCM-22), MOR type (mordenite), LTL type (L type), BEA type (beta type), and so on, and is preferably MFI type, MOR type, or BEA type. The zeolite-type compound has multiple pores with a diameter depending on its framework structure. For example, an MFI-type zeolite compound has a maximum pore size of 0.636 nm (6.36 Å) and an average pore size of 0.560 nm (5.60 Å).

The functional material 20 is in the form of fine particles, which may be primary particles or secondary particles resulting from aggregation of primary particles. The functional material 20 preferably has an average particle size $D_C$ larger than the average inner diameter $D_F$ of the channels 11. The average particle size $D_C$ of the functional material 20 is preferably equal to or smaller than the inner diameter $D_E$ of the enlarged pore portion 12. More preferably, the average particle size $D_C$ of the functional material 20 is larger than the average inner diameter $D_F$ of the channels 11 and equal to or smaller than the inner diameter $D_E$ of the enlarged pore portion 12 ($D_F < D_C \leq D_E$). The functional material 20 with such features is preferably present in the enlarged pore portion 12 in the channel 11, so that the movement of the functional material 20 is restricted in the support 10. Therefore, even when an external force is applied from a fluid to the functional material 20, the movement of the functional material 20 is suppressed in the support 10, so that pieces of the functional material 20 dispersed in channels 11 of the support 10 and respectively present in the enlarged pore portions 12 are effectively prevented from coming into contact with one another.

In the form of either primary particles or secondary particles, the functional material 20 preferably has an average particle size $D_C$ of 0.08 nm to 30 nm, more preferably 0.1 nm or more and less than 25 nm, even more preferably 0.1 nm to 11.0 nm, and further more preferably 0.1 nm to 4.0 nm. The ratio ($D_C/D_F$) of the average particle size $D_C$ of the functional material 20 to the average inner diameter $D_F$ of the channels 11 is preferably 0.05 to 300, more preferably 0.1 to 30, even more preferably 1.1 to 30, and further more preferably 1.4 to 3.6.

The functional material 20 includes a first element and a second element. The first element is one or more metal elements selected from the group consisting of cobalt (Co), nickel (Ni), iron (Fe), and ruthenium (Ru), and in particular, more preferably cobalt (Co), nickel (Ni), or iron (Fe) in terms of material costs. The second element is one or more selected from the group consisting of metal elements belonging to Groups 1, 2, 4, 7, and 12 of the periodic table. The second element used in combination with the first element in such a way can suppress the production of a silicate of the first element, so that a decrease in catalytic activity can be prevented.

In order to assist the production of the reduced form of the first element to increase catalytic active sites, the second element in the functional material 20 is preferably one or more selected from the group consisting of potassium (K), magnesium (Mg), titanium (Ti), zirconium (Zr), manganese (Mn), and zinc (Zn), and more preferably zirconium (Zr).

The functional material 20 may include metal fine particles including one or both of the first and second elements. In this case, a single metal element may be used as the first or second element, or two or more metal elements may be used as the first or second elements. Two or more metal elements may form a mixture or at least partially form an alloy. For example, the functional material 20 may include an alloy including the first and second elements or include a composite material of the first and second elements, as long as the functional material 20 can have the metallic state when used as a catalyst. The functional material 20 may also include metal oxide fine particles including one or both of an oxide of the first element and an oxide of the second element. Before the metal oxide fine particles are used, the metal oxide may be reduced into metal by a reducing step (step S5) described later or by being exposed to a reducing atmosphere-containing usage environment for a certain period of time, so that the resulting metal can be used as a catalyst. When used herein to indicate the component (material) of the functional material for use as a catalyst, the term "metal" is a generic term for a metallic material including one or more metal elements, which is intended to include an elementary metal including a single metal element and a metal mixture and alloy including two or more metal elements.

In particular, the metal fine particles present as the functional material 20 preferably include one or both of: alloy fine particles including the first and second elements; and two or more types of single metal fine particles, which include metal fine particles including the first element and metal fine particles including the second element. The functional material 20 may include both of alloy fine particles and single metal fine particles. For example, the functional material 20 may be in the form of fine particles including the second element supported on fine particles including the first element, in the form of an alloy including the first and second elements, or in the form of composite fine particles including the first and second elements.

The mass ratio of the content of the second element to the content of the first element is preferably 0.01 to 2.00 and more preferably 0.02 to 1.50. The catalyst structure 1 according to the present invention can resist a decrease in catalytic activity even when the content of the second element is relatively low. In the catalyst structure 1, the content of the second element is preferably lower than the content of the first element.

The catalyst structure 1 preferably has a total content of the first element of 0.5% by mass or more with respect to the mass of the catalyst structure 1. The upper limit of the total content of the first element of the catalyst structure 1 is preferably, but not limited to, 7.6% by mass or less, more preferably 6.9% by mass, even more preferably 2.5% by mass, and most preferably 1.5% by mass. For example, when the first element is Co, the content (% by mass) of the Co element is expressed by {(the mass of Co element)/(the mass of all elements in the catalyst structure 1)}×100.

The catalyst structure 1 preferably has a total second element content of 5% by mass or less, more preferably 0.01 to 0.15% by mass, and even more preferably 0.02 to 0.10% by mass, with respect to the mass of the catalyst structure 1.

Besides the first and second elements, the functional material may further include a third element. Examples of the third element include platinum (Pt), palladium (Pd), gold (Au), copper (Cu), ruthenium (Ru), iridium (Ir), rhodium (Rh), and osmium (Os). The addition of such a third element can further suppress a decrease in catalytic activity. The mechanism to suppress a decrease in catalytic activity may be that the third element can cause spill-over of hydrogen, which would promote the production of the reduced form of the first element. In order to prevent a decrease in catalytic activity due to a decrease in the relative content of the first and second elements, the content of the third element is preferably 0.27% by mass or less with respect to the mass of the catalyst structure 1.

Function of Catalyst Structure

As mentioned above, the catalyst structure 1 includes a support 10 of a porous structure and at least one functional material 20 in the support 10. When brought into contact with a fluid, the catalyst structure 1 exerts the catalytic ability of the functional material 20 in the support. Specifically, when coming into contact with the outer surface 10a of the catalyst structure 1, the fluid is allowed to flow into the interior of the support 10 through a pore 11a at the outer surface 10a, guided into the channels 11, and allowed to pass through the channels 11 and to flow out of the catalyst structure 1 through another pore 11a. The functional material 20 in the channel 11 causes a catalytic reaction when coming into contact with the fluid passing through the channel 11. The catalyst structure 1 also has a molecular sieving ability since the support has a porous structure.

Figure 2A:
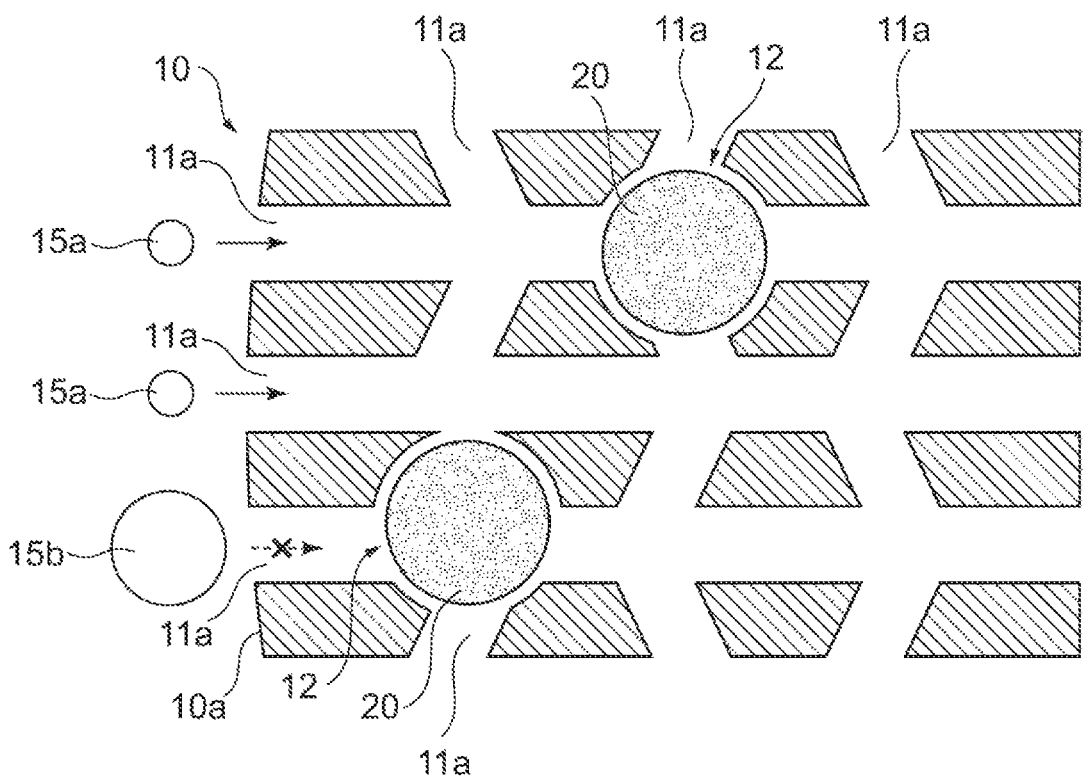

First, the molecular sieving ability of the catalyst structure 1 will be described regarding FIG. 2A. As shown in FIG. 2A, molecules 15a having a size equal to or smaller than the diameter of the pore 11a, in other words, equal to or smaller than the inner diameter of the channel 11, can enter the support 10. On the other hand, a molecule 15b having a size exceeding the diameter of the pore 11a cannot enter the support 10. Accordingly, among multiple compounds in the fluid, some compounds not capable of entering the support 10 are restricted from reacting, and some other compounds capable of entering the support 10 are allowed to react.

Among compounds produced by reactions in the support 10, only compounds having a molecular size not exceeding the diameter of the pore 11a can go outside the support 10 through the pore 11a to give a reaction product. On the other hand, some compounds are not capable of going outside the support 10 through the pore 11a. If such compounds are converted into compounds having a molecular size that allows exit from the support 10, the compounds can go outside the support 10. As a result, the use of the catalyst structure 1 makes it possible to selectively obtain a specific reaction product.

Figure 2B:
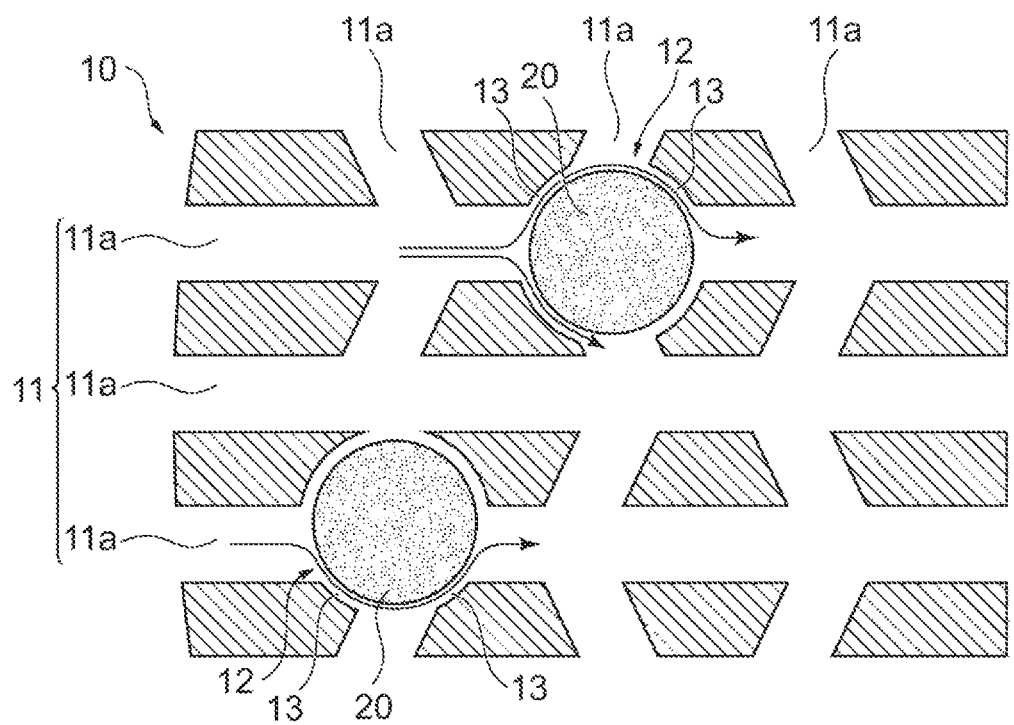

In the catalyst structure 1, the functional material 20 is enclosed in the enlarged pore portion 12 of the channel 11 as shown in FIG. 2B. When the average particle size $D_C$ of the functional material 20 is larger than the average inner diameter $D_F$ of the channel 11 and smaller than the inner diameter $D_E$ of the enlarged pore portion 12 ($D_F<D_C<D_E$), a small channel 13 is provided between the functional material and the enlarged pore portion 12. In this case, as indicated by the arrow in FIG. 2B, the fluid entering the small channel 13 comes into contact with the functional material. Each piece of the functional material enclosed in the enlarged pore portion 12 is restricted from moving in the support 10. Thus, fine particles of the functional material are prevented from aggregating in the support 10. As a result, a large contact area can be stably maintained between the functional material and the fluid.

In particular, the second element contained together with the first element in the catalyst structure 1 can suppress the production of a silicate of the first element, which has high catalytic activity in the metallic state, so that a decrease in catalytic activity can be prevented.

Specifically, when a molecule (a material to be reformed) entering the channel 11 comes into contact with the functional material 20, a catalytic reaction occurs to reform the molecule. According to the present invention using the catalyst structure 1, for example, hydrocarbons (excluding $CH_4$), preferably $C_2$ to $C_{20}$ hydrocarbons, can be produced from a raw material of a gas mixture composed mainly of hydrogen and carbon monoxide. In particular, hydrocarbons including $C_2$ to $C_5$ lower hydrocarbons can also be produced using the catalyst structure 1 according to the present invention. The catalytic reaction, although carried out, for example, at a high temperature of 180° C. to 350° C., is less affected by the heating, since the functional material 20 is incorporated in the support 10. In particular, the functional material 20 inside the enlarged pore portion 12 is more restricted from moving in the support 10, so that fine particles of the functional material 20 are more effectively prevented from aggregating (sintering). As a result, a decrease in catalytic activity is more effectively prevented, which allows the catalyst structure 1 to have a longer life. During the long-term use of the catalyst structure 1, the functional material 20 can be easily treated (reduced) for activation even when its catalytic activity is reduced.

Method of Producing Catalyst Structure

Figure 3:
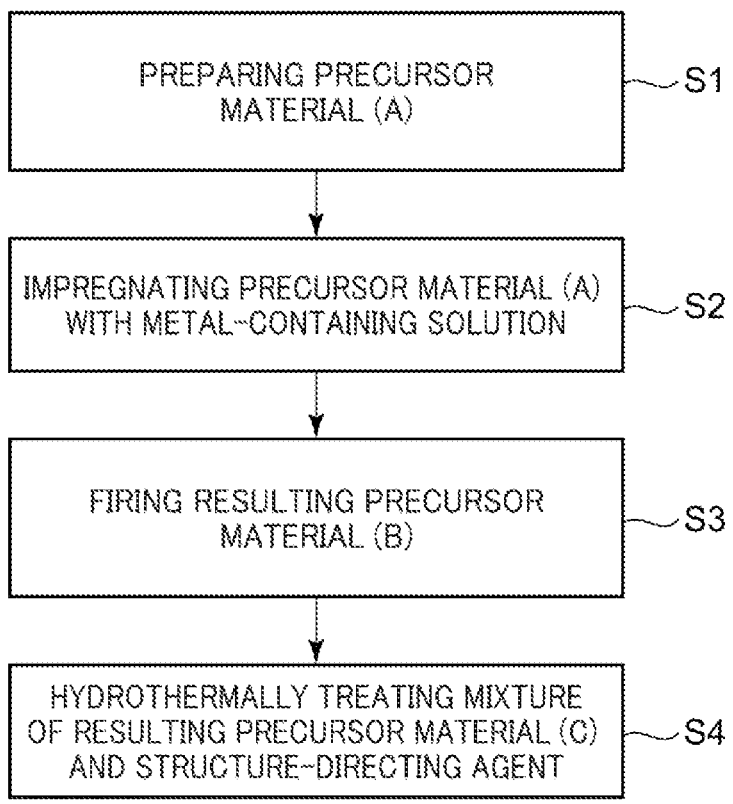
FIG. 3 is a flowchart showing an example of a method of producing the catalyst structure of FIGS. 1A and 1B.

FIG. 3 is a flowchart showing a method of producing the catalyst structure 1 of FIGS. 1A and 1B.

Step S1: Preparation Step

As shown in FIG. 3, first, a precursor material (A) is prepared, which is for forming a support having a porous structure and including a zeolite-type compound. The precursor material (A) is preferably an ordered mesoporous material, and may be appropriately selected depending on the type (composition) of the zeolite-type compound for forming the support of the catalyst structure.

When a silicate compound is used as the zeolite-type compound for forming the support of the catalyst structure, the ordered mesoporous material is preferably a compound having an Si—O framework having pores with a diameter of 1 to 50 nm uniformly and regularly developed in a one-, two-, or three-dimensional pattern. A variety of synthetic products can be obtained as such ordered mesoporous materials depending on the synthesis conditions. Examples of such synthetic products include SBA-1, SBA-15, SBA-16, KIT-6, FSM-16, and MCM-41. In particular, MCM-41 is preferred. For reference, SBA-1 has a pore size of 10 to 30 nm, SBA-15 has a pore size of 6 to 10 nm, SBA-16 has a pore size of 6 nm, KIT-6 has a pore size of 9 nm, FSM-16 has a pore size of 3 to 5 nm, and MCM-41 has a pore size of 1 to 10 nm. Examples of such an ordered mesoporous material include mesoporous silica, mesoporous aluminosilicate, and mesoporous metallosilicate.

The precursor material (A) may be any of a commercially available product and a synthetic product. The precursor material (A) may be synthesized using a known method for synthesizing an ordered mesoporous material. For example, a mixture solution is prepared, which contains a raw material containing the element for forming the precursor material (A) and a template agent for directing the structure of the precursor material (A). Optionally after being subjected to pH adjustment, the mixture solution is subjected to hydrothermal treatment (hydrothermal synthesis). Subsequently, the precipitate (product) resulting from the hydrothermal treatment is collected (e.g., filtered off), washed and dried if necessary, and then fired to give a precursor material (A) as a powdery ordered mesoporous material. In this process, the solvent for the mixture solution may be, for example, water, an organic solvent such as an alcohol, or a mixed solvent thereof. The raw material may be selected depending on the type of the support. Examples of the raw material include silica agents, such as tetraethoxysilane (TEOS), fumed silica, and quartz sand. The template agent may be any of various surfactants and block copolymers. The template agent is preferably selected depending on the type of the ordered mesoporous material to be synthesized. For example, the template agent for use in forming MCM-41 is preferably a surfactant such as hexadecyltrimethylammonium bromide or polyoxyethylene (15) oleyl ether. Alternatively, the template agent may not be used. The hydrothermal treatment may be performed, for example, in a closed vessel under conditions at 80 to 800° C. and 0 to 2,000 kPa for 5 hours to 240 hours. The firing treatment may be performed, for example, in the air under conditions at 350 to 850° C. for 2 to 30 hours.

Step S2: Impregnation Step

Next, the prepared precursor material (A) is impregnated with a metal-containing solution containing the first and second metal elements to form a precursor material (B).

The metal-containing solution may be any solution containing metal components (e.g., metal ions) corresponding to the first element ($M_1$) and the second element ($M_2$) for forming the functional material of the catalyst structure. For example, the metal-containing solution may be prepared by dissolving, in a solvent, metal salts containing the first element ($M_1$) and the second element ($M_2$). Examples of such metal salts include chlorides, hydroxides, oxides, sulfates, and nitrates, among which chlorides or nitrates are preferred. The solvent may be, for example, water, an organic solvent such as an alcohol, or a mixture solvent thereof.

Any method may be used to impregnate the precursor material (A) with the metal-containing solution. For example, before the firing step described later, the impregnation is preferably performed by adding the metal-containing solution little by little in multiple portions to the powdery precursor material (A) being stirred. In order to allow the metal-containing solution to more easily enter the inner pores of the precursor material (A), a surfactant is preferably added as an additive in advance before the addition of the metal-containing solution. Such an additive can act to cover the outer surface of the precursor material (A) and thus to inhibit the deposition of the metal-containing solution on the outer surface of the precursor material (A), so that the metal-containing solution added subsequently could easily enter the pores of the precursor material (A).

Examples of such an additive include nonionic surfactants, such as polyoxyethylene oleyl ether, polyoxyethylene alkyl ether, and polyoxyethylene alkyl phenyl ether. These surfactants have a large molecular size and thus cannot enter the inner pores of the precursor material (A), which suggests that they will not adhere to the interior of the pores and will not hinder the entrance of the metal-containing solution into the pores. A method of adding the nonionic surfactant preferably includes, for example, adding 50 to 500% by mass of the nonionic surfactant to the precursor material (A) before the firing step described later. If the amount of the nonionic surfactant added to the precursor material (A) is less than 50% by mass, the inhibiting effect may be difficult to achieve, and if the amount of the nonionic surfactant added to the precursor material (A) is more than 500% by mass, undesirably high viscosity may be reached. Therefore, the amount of the nonionic surfactant added to the precursor material (A) should be set to a value within the above range.

The amount of the first element ($M_1$) in the metal-containing solution, with which the precursor material (A) is to be impregnated (in other words, the amount of the first element ($M_1$) to be incorporated into the precursor material (B)) is preferably taken into account when the amount of the metal-containing solution added to the precursor material (A) is appropriately adjusted. In the precursor material (B), the content of the first element ($M_1$) and the second element ($M_2$) in the inner porous portion is approximately proportional to the amount of the metal-containing solution added to the precursor material (A) as long as the metal concentration of the metal-containing solution, the presence or absence of the additive, and other conditions such as temperature and pressure remain constant. The amount of the first element ($M_1$) and the second element ($M_2$) in the precursor material (B) is also proportional to the amount of the first element ($M_1$) and the second element ($M_2$) in the functional material in the support of the catalyst structure. Accordingly, when the amount of the metal-containing solution added to the precursor material (A) is controlled within the above range, the inner pores of the precursor material (A) can be impregnated with a sufficient amount of the metal-containing solution, which makes it possible to adjust the content of the functional material in the support of the catalyst structure.

When the precursor material (A) is impregnated with the metal-containing solution before the firing step described later, the amount of the metal-containing solution added to the precursor material (A) is preferably adjusted such that the ratio (Si/$M_1$ atomic ratio) of the number of silicon (Si) atoms in the precursor material (A) to the number of the first element ($M_1$) atoms in the metal-containing solution is set to 10 to 1,000, more preferably 30 to 300, and even more preferably 50 to 200. If the ratio is more than 1,000, the functional material may fail to have a sufficient level of catalytic performance or may have low activity. If the ratio is less than 10, the content of the functional material 20 may be too high so that the support 10 may tend to have reduced strength. For example, when a surfactant is added as an additive to the precursor material (A) before the addition of the metal-containing solution to the precursor material (A), the amount of the metal-containing solution added to the precursor material (A) may be adjusted such that the calculated Si/$M_1$ atomic ratio can be 50 to 200. In such a case, the total content of the first element ($M_1$) in the functional material can be adjusted to 0.5 to 7.6% by mass with respect to the mass of the catalyst structure. It should be noted that, in this context, the functional material 20 refers to fine particles held or supported inside the support 10 and does not include a functional material deposited on the outer surface of the support 10.

When the precursor material (A) is impregnated with the metal-containing solution before the firing step described later, the amount of the metal-containing solution added to the precursor material (A) is preferably adjusted such that the ratio (Si/$M_2$ atomic ratio) of the number of silicon (Si) atoms for forming the support 10 to the number of the second element ($M_2$) atoms in the metal-containing solution is set to 1,000 to 10,000 and more preferably 1,000 to 7,000. If the ratio is more than 10,000, the second element may fail to be sufficiently effective in preventing a decrease in catalytic activity. If the ratio is less than 1,000, the content of the first element 20 may be relatively low so that the catalytic activity may rather tend to decrease. It should be noted that, in this context, the functional material 20 refers to fine particles held or supported inside the support 10 and does not include a functional material deposited on the outer surface of the support 10.

After the precursor material (A) is impregnated with the metal-containing solution, washing treatment may be performed if necessary. The washing liquid used may be water, an organic solvent such as an alcohol, or a mixed solution thereof. Drying treatment is also preferably performed after the impregnation of the precursor material (A) with the metal-containing solution and optionally after the washing treatment. The drying treatment may include natural drying overnight or so or drying at a high temperature of 150° C.

or less. The drying is preferably performed thoroughly because the framework structure of the precursor material (A) for the ordered mesoporous material may collapse if the firing treatment described later is performed while a large amount of water derived from the metal-containing solution or the washing liquid remains in the precursor material (A).

Step S3: Firing Step

Next, the precursor material (B) is fired to form a precursor material (C). The precursor material (B) is a product obtained through impregnating, with the metal-containing solution, the precursor material (A) for forming the support having a porous structure and including the zeolite-type compound.

The firing is preferably carried out, for example, in the air under conditions at 350 to 850° C. for 2 to 30 hours. Such firing treatment allows the growth of crystals of the metal component deposited by the impregnation in the pores for the ordered mesoporous material, so that the functional material is formed in the pores.

Step S4: Hydrothermal Treatment Step

Then, the precursor material (C), obtained through firing the precursor material (B), and a structure-directing agent are mixed to form a mixture solution, which is hydrothermally treated to form a catalyst structure.

The structure-directing agent is a template agent for directing the framework structure of the skeleton (support) of the catalyst structure. The structure-directing agent may be at least one of an organic structure-directing agent (in general abbreviated as "OSDA") and an OH⁻-containing inorganic structure-directing agent. The organic structure-directing agent may be, for example, a surfactant. The organic structure-directing agent is preferably selected depending on the framework structure of the support in the catalyst structure, and preferred examples thereof include tetramethylammonium bromide (TMABr), tetraethylammonium bromide (TEABr), tetrapropylammonium bromide (TPABr), tetraethylammonium hydroxide (TEAOH), and other surfactants. Typical examples of the inorganic structure-directing agent include hydroxides of alkali metals and alkaline earth metals, such as lithium hydroxide (LiOH), sodium hydroxide (NaOH), potassium hydroxide (KOH), rubidium hydroxide (Rb(OH)), calcium hydroxide ($Ca(OH)_2$), and strontium hydroxide ($Sr(OH)_2$).

The precursor material (C) and the structure-directing agent may be mixed during or before the hydrothermal treatment step. Any method may be used to prepare the mixture solution. The precursor material (C), the structure-directing agent, and the solvent may be mixed at the same time, or the precursor material (C) and the structure-directing agent may be separately dispersed into individual solvents, and then the resulting dispersion solutions may be mixed. The solvent may be, for example, water, an organic solvent such as an alcohol, or a mixed solvent thereof. Before the hydrothermal treatment, the mixture solution is preferably subjected to pH adjustment using an acid or a base.

The hydrothermal treatment may be carried out using a known method, which is preferably performed in a closed vessel under conditions at 80 to 800° C. and 0 to 2,000 kPa for 5 hours to 240 hours. The hydrothermal treatment is also preferably performed in a basic atmosphere. Although the reaction mechanism is not necessarily clear, the hydrothermal treatment using the precursor material (C) as a starting material can gradually destroy the framework structure of the precursor material (C) for the ordered mesoporous material but can form a new framework structure (porous structure) for the support of the catalyst structure due to the action of the structure-directing agent while the position of the functional material in the pores of the precursor material (C) substantially remains. The resulting catalyst structure includes a support of a porous structure and a functional material present in the support and including the first and second elements, in which the support has channels connecting multiple pores derived from the porous structure, and at least some of the functional material is located in channels of the support. In the embodiment, the hydrothermal treatment step includes preparing a solution of a mixture of the precursor material (C) and the structure-directing agent and hydrothermally treating the precursor material (C) in the mixture solution. This step is non-limiting, and alternatively, the precursor material (C) may be hydrothermally treated without being mixed with the structure-directing agent.

Preferably, the precipitate (catalyst structure) resulting from the hydrothermal treatment is collected (e.g., filtered off) and then optionally washed, dried, and fired. The washing liquid may be water, an organic solvent such as an alcohol, or a mixed solution thereof. The drying may include natural drying overnight or so or drying at a high temperature of 150° C. or less. The drying is preferably performed thoroughly because the framework structure for the support of the catalyst structure may collapse if the firing treatment is performed while a large amount of water remains in the precipitate. The firing treatment may be performed, for example, in the air under conditions at 350 to 850° C. for 2 to 30 hours. During such firing treatment, the structure-directing agent is burned away from the catalyst structure. Depending on the intended use, the catalyst structure may be used as it is without undergoing the firing treatment of the collected precipitate. For example, when the catalyst structure is used in a high-temperature oxidative atmosphere environment, the structure-directing agent will be burned away by being exposed to the usage environment for a certain period of time. In such a case, the resulting catalyst structure can used without any modification since it is substantially the same as that obtained after the firing treatment.

The production method described above may be an example in which the first element ($M_1$) or the second element (142) in the metal-containing solution for impregnation of the precursor material (A) is an oxidation-resistant metal species (e.g., noble metal Ru).

Step S5: Reduction Step

After the hydrothermal treatment step, the hydrothermally treated precursor material (C) is preferably subjected to reduction treatment. For example, when the metal-containing solution contains, as the first element ($M_1$), at least one of Co, Fe, and Ni, which are metal species vulnerable to oxidation, the metal component can be oxidized by heating in the steps (S3 and S4) after the impregnation step (S2). Accordingly, the support formed in the hydrothermal treatment step (S4) may contain metal oxide fine particles as a functional material. In order to obtain a catalyst structure including a support containing metal fine particles, the hydrothermal treatment is preferably followed by optional firing treatment of the collected precipitate and then preferably followed by reduction treatment in a reducing gas atmosphere, such as hydrogen gas. The reduction treatment reduces metal oxide fine particles in the support to form metal fine particles, which correspond to the metal element in the metal oxide fine particles. As a result, a catalyst structure is obtained including a support containing metal fine particles as a functional material. In this reduction step, the degree of reduction may be controlled to prevent or control a decrease in the function of the catalyst structure containing metals and metal oxides. It should be noted that such reduction treatment may be performed as needed. For example, if the catalyst structure is used at least temporarily in a reducing atmosphere environment, the metal oxide fine particles can be reduced by being exposed to the usage environment containing a reducing atmosphere for a certain period of time. In such a case, the catalyst structure in which the support contains oxide fine particles may be used as it is, since the catalyst structure obtained after the exposure to the usage environment is substantially the same as that obtained after the reduction treatment.

Modifications of Catalyst Structure

Figure 4:
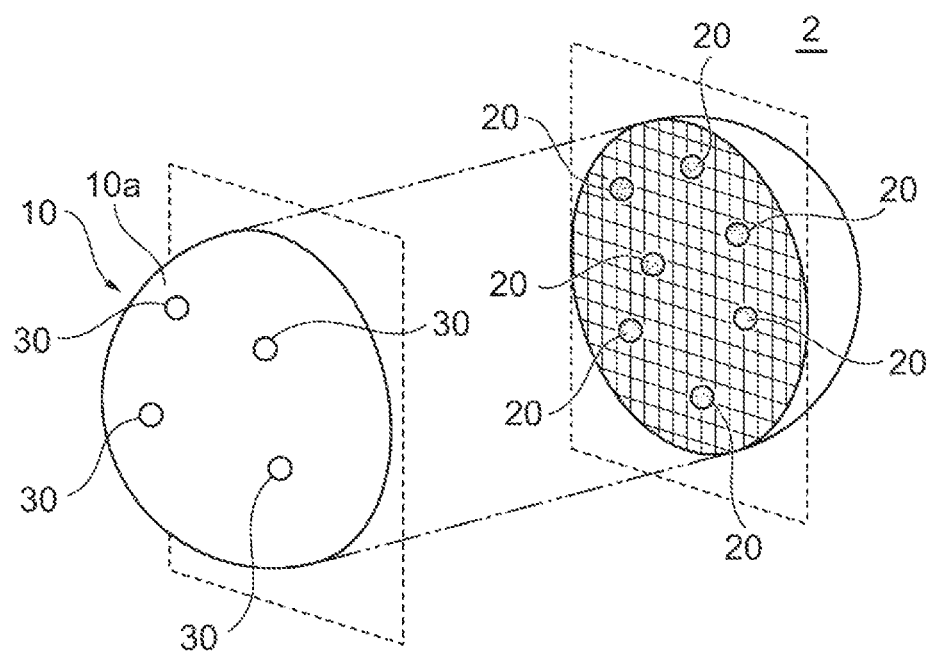
FIG. 4 is a schematic view showing a modification of the catalyst structure of FIGS. 1A and 1B.

FIG. 4 is a schematic view showing a modification of the catalyst structure 1 of FIGS. 1A and 1B. The catalyst structure 1 shown in FIGS. 1A and 1B includes the support 10 and the functional material 20 in the support 10. Such a structure is non-limiting, and, as shown in FIG. 4, for example, a catalyst structure 2 may be provided, which further includes an additional functional material 30 held on an outer surface 10a of the support 10.

When used at least as a catalyst, the functional material 30 can exert one or more types of catalytic abilities. The catalytic ability of the additional functional material 30 may be the same as or different from that of the functional material 20. The functional material 30 having the same catalytic ability as that of the functional material 20 may be the same as or different from the functional material 20. According to this feature, the catalyst structure 2 can have an increased functional material content, which further enhances the catalytic activity of the functional material.

Specifically, like the functional material 20, the additional functional material 30 may include one or more metals selected from the group consisting of cobalt (Co), nickel (Ni), iron (Fe), and ruthenium (Ru), corresponding to the first element, or an alloy thereof. Alternatively, like the functional material 20, the additional functional material may include at least one of metals belonging to Groups 1, 2, 4, 7, and 12 of the periodic table, or an alloy thereof. In particular, when the additional material 30 also includes elements corresponding to the first and second elements, the second element can suppress the production of a silicate of the first element, so that a decrease in the catalytic activity of the additional functional material 30 can also be prevented.

In this case, the content of the functional material 20 in the support 10 is preferably higher than the content of the additional functional material 30 held on the outer surface 10a of the support 10. In such a case, the catalytic ability of the functional material 20 held inside the support 10 can be dominant, and the functional materials can stably exhibit their functional ability. Particularly in such a case, the functional material 20 held inside the support 10 of the catalyst structure 2 is less likely to separate from the support 10 and to aggregate than the additional functional material 30 held on the outer surface 10a of the support 10, and thus the content of the functional material 20 will be higher than that of the additional functional material 30 regardless of the period of time for which the catalyst is used.

Modifications of Method of Producing Catalyst Structure

FIG. 3 shows a non-limiting example of the method of producing the catalyst structure 1, which includes impregnating the precursor material (A) with a metal-containing solution including the first and second metal elements. Alternatively, for example, the method may include performing step S2 (impregnation step) which includes impregnating the precursor material (A) with a metal-containing solution (first element-containing solution) containing the first element; subjecting the impregnated precursor material (A) to step S3 (first firing step); performing step S4 (hydrothermal treatment step); optionally performing step S5 (reduction step) to allow the catalyst structure 1 to contain the functional material 20; then impregnating, with a solution containing the second element, a precursor material (D) including the hydrothermally-treated precursor material (C); firing the precursor material (D) impregnated with the second element-containing solution (second firing step); and optionally reducing the precursor material (D), having been fired, to deposit the additional functional material 30 on the outer surface 10a of the support 10. This method yields a catalyst structure that contains the functional material 20 in the support 10 and holds the additional functional material 30 on the outer surface 10a of the support 10.

In this method, any method may be used to impregnate the hydrothermally-treated precursor material (C) with the second element-containing solution. For example, the same method may be used as in the impregnation of the precursor material (A) with the metal-containing solution.

The precursor material (D) impregnated with the second element-containing solution may also be fired in the same manner as in the firing of the precursor material (A) impregnated with the metal-containing solution. After the firing, the precursor material (D) may also be subjected to reduction treatment.

Applications of Catalyst Structure

In particular, the catalyst structure of the present invention is suitable for use in chemical reactions that involve functional material oxidation that could reduce catalytic activity.

Production of Hydrocarbons by FT Synthesis Reaction

As an example of the application, a method of producing hydrocarbons is provided, which includes carrying out an FT synthesis reaction using the catalyst structure of the present invention to synthesize hydrocarbons from carbon monoxide and hydrogen. The catalyst used in such a method is a catalyst structure 1 including: a support 10 that has a porous structure and includes a zeolite-type compound; and at least one functional material 20 present in the support 10 and including the first element and the second element, in which the support 10 has channels 11 communicating with one another, and the functional material 20 is present at least in an enlarged pore portion 12 of the channel 11 in the support 10. Specifically, the present invention provides a method of producing hydrocarbons, which includes using the catalyst structure described above to synthesize hydrocarbons from carbon monoxide and hydrogen. In the method using the catalyst structure described above, an FT synthesis reaction-induced decrease in catalytic activity can be prevented because the functional material used as a catalyst can be prevented from being oxidized by water ($H_2O$) molecules as a by-product of the FT synthesis reaction.

The raw material for use in the method of producing hydrocarbons using such Fischer-Tropsch synthesis reaction may be any syngas composed mainly of molecular hydrogen and carbon monoxide. Such a syngas preferably has a hydrogen/carbon monoxide molar ratio of 1.5 to 2.5 and more preferably 1.8 to 2.2. The FT synthesis reaction may also be carried out under any known conditions. For example, the reaction is preferably carried out at a temperature of 200 to 500° C. and a pressure (absolute pressure) of 0.1 to 3.0 MPa.

The Fischer-Tropsch synthesis reaction may be carried out according to a known reaction process using, for example, a fixed bed, a supercritical fixed bed, a slurry bed, a fluidized bed, or the like. The process preferably uses a fixed bed, a supercritical fixed bed, or a slurry bed.

The present invention may also provide a hydrocarbon production system including the catalyst structure described above. Such a hydrocarbon production system may be any type that allows Fischer-Tropsch synthesis using the catalyst structure described above. For example, the system may be an FT synthesis reaction system, an FT synthesis reaction column, or any other production system generally used in the art. Such a hydrocarbon production system using the catalyst structure according to the present invention brings about the same advantageous effects as those described above.

While a catalyst structure, a method of producing the catalyst structure, a method of producing hydrocarbons using the catalyst structure, and a hydrocarbon production system including the catalyst structure according to embodiments of the present invention have been described, it will be understood that the embodiments are not intended to limit the present invention and may be altered or modified in various ways based on the technical idea of the present invention. Production of Syngas by Partial Oxidation Reaction The present invention also provides a method of producing a syngas, which includes carrying out a partial oxidation reaction using the catalyst structure of the present invention to synthesize carbon monoxide and hydrogen from methane. The catalyst used in such a method is a catalyst structure 1 including: a support 10 that has a porous structure and includes a zeolite-type compound; and at least one functional material 20 present in the support 10 and including the first element and the second element, in which the support 10 has channels 11 communicating with one another, and the functional material 20 is present at least in an enlarged pore portion 12 of the channel 11 in the support 10. Specifically, the present invention provides a method of producing a syngas, which includes using the catalyst structure described above to synthesize carbon monoxide and hydrogen from methane.

In the method using the catalyst structure described above, a partial oxidation reaction-induced decrease in catalytic activity can be prevented because the functional material can be prevented from being oxidized by oxygen (OA molecules supplied for oxidation of methane.

EXAMPLES

Examples 1 to 4, 6 to 14

Synthesis of Precursor Material (A)

An aqueous solution of a mixture of a silica agent (tetraethoxysilane (TEOS) manufactured by Wako Pure Chemical Industries, Ltd.) and a surfactant as a template agent was prepared, then subjected to pH adjustment as needed, and then hydrothermally treated in a closed vessel at 80 to 350° C. for 100 hours. Subsequently, the produced precipitate was filtered off, then washed with water and ethanol, and then fired in air at 600° C. for 24 hours to give a precursor material (A) of the type and pore size shown in Table 1. The following surfactant was used according to the type of the precursor material (A) (see "Type of Precursor Material (A)" for surfactant). For MCM-41: Hexadecyltrimethylammonium bromide (CTAB) (manufactured by Wako Pure Chemical Industries, Ltd.) Preparation of Precursor Materials (B) and (C)

Next, depending on the type of the metal component of the functional material shown in Table 2, metal salts containing a first metal element and a second metal element were dissolved in water to form a metal-containing aqueous solution. The following metal salts were used according to the type of metal fine particles constituting the functional material (see "Metal fine particles" for metal salt). First Element For Co: Cobalt(II) nitrate hexahydrate (manufactured by Wako Pure Chemical Industries, Ltd.)

For Ni: Nickel(II) nitrate hexahydrate (manufactured by Wako Pure Chemical Industries, Ltd.)

For Fe: Iron(III) nitrate nonahydrate (manufactured by Wako Pure Chemical Industries, Ltd.)

For Ru: Ruthenium(III) chloride anhydrous (manufactured by Tokyo Chemical Industry Co., Ltd.) Second Element For Zr: Zirconium(IV) nitrate (manufactured by Wako Pure Chemical Industries, Ltd.)

A pretreatment was performed in which an aqueous solution of polyoxyethylene (15) oleyl ether (NIKKOL BO-15V, manufactured by Nikko Chemicals Co., Ltd.) as an additive (nonionic surfactant) was added to the powdery precursor material (A). Subsequently, the metal-containing aqueous solution was added little by little in multiple portions to the powdery precursor material (A), and the resulting product was then dried at room temperature (20° C.±10° C.) for at least 12 hours to give a precursor material (B).

The amount of the metal-containing aqueous solution added to the precursor material (A) was adjusted such that the calculated ratio (Si/$M_1$ atomic ratio) of the silicon (Si) content of the precursor material (A) to the first element ($M_1$) content of the metal-containing aqueous solution and the calculated ratio (Si/$M_2$ atomic ratio) of the silicon (Si) content of the precursor material (A) to the second element ($M_2$) content of the metal-containing aqueous solution were as shown in Table 1.

Subsequently, the resulting precursor material (B) impregnated with the metal-containing aqueous solution was fired in air at 600° C. for 24 hours to give a precursor material (C).

An aqueous solution of a mixture of the resulting precursor material (C) and a structure-directing agent shown in Table 1 was prepared and then hydrothermally treated in a closed vessel at 80 to 350° C. under the pH and time conditions shown in Table 1. Subsequently, the produced precipitate was filtered off, then washed with water, then dried at 100° C. for at least 12 hours, and then fired in air at 600° C. for 24 hours. Subsequently, the firing product was collected and then subjected to reduction treatment under hydrogen gas stream at 500° C. for 60 minutes to give a catalyst structure including a support and metal fine particles as a functional material as shown Table 1 (Examples 1 to 4 and 6 to 14).

Example 5

Synthesis of Precursor Material (A)

A precursor material (A) of the type and pore size shown in Table 1 was obtained using a process similar to that in Examples 1 to 4 and 6 to 14.
Preparation of Precursor Materials (B) and (C)

Next, depending on the type of the first element for forming metal fine particles of the functional material shown in Table 2, a metal salt containing the first element was dissolved in water to form a first element-containing aqueous solution. In this process, cobalt(II) nitrate hexahydrate (manufactured by Wako Pure Chemical Industries, Ltd.) was used as the metal salt.

Subsequently, the first element-containing aqueous solution was added little by little in multiple portions to the powdery precursor material (A) and then dried at room temperature (20° C.±10° C.) for at least 12 hours to give a precursor material (B).

In this process, the amount of the first element-containing aqueous solution added to the precursor material (A) was adjusted such that the calculated ratio (Si/$M_1$ atomic ratio) of the silicon (Si) content of the precursor material (A) to the first element ($M_1$) content of the first element-containing aqueous solution was as shown in Table 1.

Subsequently, the resulting precursor material (B) impregnated with the first element-containing aqueous solution was fired in air at 600° C. for 24 hours to give a precursor material (C).

An aqueous solution of a mixture of the resulting precursor material (C) and a structure-directing agent shown in Table 1 was prepared and then hydrothermally treated in a closed vessel at 80 to 350° C. under the pH and time conditions shown in Table 1. Subsequently, the produced precipitate was filtered off, then washed with water, then dried at 100° C. for at least 12 hours, and then fired in air at 600° C. for 24 hours. The resulting precursor material (D) was collected.

Next, a second element-containing metal salt was dissolved in water to form a second element-containing aqueous solution. The metal salt used was zirconium(IV) nitrate (manufactured by Wako Pure Chemical Industries, Ltd.). The amount of the second element-containing aqueous solution added to the precursor material (D) was adjusted such that the calculated ratio (Si/$M_2$ atomic ratio) of the silicon (Si) content of the precursor material (D) to the second element ($M_2$) content of the second element-containing aqueous solution was as shown in Table 1. The second element-containing aqueous solution was added little by little in multiple portions to the collected precursor material (D). The resulting product was dried at room temperature (20° C.±10° C.) for at least 12 hours and then fired in air at 600° C. for 24 hours. Subsequently, the firing product (F) was collected and subjected to reduction treatment under hydrogen gas stream at 500° C. for 60 minutes to give a catalyst structure including a support and metal fine particles as a functional material as shown in Table 1 (Example 5). Cross-sectional elemental analysis using scanning electron microscopy (SEM) and energy-dispersive X-ray spectroscopy (EDX) revealed that the catalyst structure of Example 5 contained, in the support, the functional material including cobalt as the first element and held zirconium as the second element on the outer surface of the support.

Comparative Example 1

In Comparative Example 1, a mixture of MFI silicalite and cobalt oxide powder (II, III manufactured by Sigma-Aldrich Japan) with an average particle size of at most 50 nm was impregnated with zirconium(IV) nitrate (manufactured by Wako Pure Chemical Industries, Ltd.). The resulting product was dried at room temperature (20° C.±10° C.) for at least 12 hours and then fired in air at 600° C. for 24 hours. The product was subjected to hydrogen reduction treatment in a similar manner to the examples, so that a catalyst structure was obtained including: cobalt fine particles deposited as a functional material on the outer surface of silicalite as a support; and supported zirconium particles.

The MFI silicalite was synthesized in the same manner as in Example 1, except for the step of adding the metal.

Comparative Example 2

In Comparative Example 2, MFI silicalite was synthesized in the same manner as in Comparative Example 1, except that the step of depositing cobalt fine particles was omitted.

Evaluation

The catalyst structures of the examples and the silicalites of the comparative examples were evaluated for characteristics under the conditions shown below.

(A) Cross-Sectional Observation

Samples for observation were prepared by grinding technique from the catalyst structures of the examples and the silicalites of the comparative examples. The cross-section of each sample was observed using a transmission electron microscope (TEM) (TITAN G2 manufactured by FEI Company). As a result, in the catalyst structure of each of the examples, metal fine particles for serving as a functional material (catalytic material) were found to be located and held inside the support composed of silicalite or zeolite. On the other hand, in the silicalite of Comparative Example 1, the functional material was found to be deposited only on the outer surface of the support and not found inside the support.

Among the catalyst structures of the examples, the catalyst structures containing metal fine particles including Fe and Zr as the first and second elements, respectively, were subject to cross-section cutting using focused ion beam (FIB). The resulting cross-sections were subjected to elemental analysis using SEM (SU8020 manufactured by Hitachi High Technologies Co., Ltd.) and EDX (X-Max manufactured by Horiba, Ltd.). As a result, Fe and Zr elements were detected from the inside of the support. The results of the cross-sectional observation using TEM and SEM/EDX revealed the existence of metal fine particles inside the support.

(B) Average Inner Diameter of Channels of Support and Average Particle Size of Functional Material Any 500 channels of the support were selected in the TEM image taken during the cross-sectional observation performed for the evaluation (A). The long and short diameters of each of the channels were measured. The measurements were averaged to calculate the inner diameter of each channel (N=500), and the calculated inner diameters were averaged as the average inner diameter $D_F$ of the channels of the support.

Small angle X-ray scattering (SAXS) analysis was also performed to determine the average particle size and dispersed state of the catalytic material. The SAXS measurement was carried out using the beamline BL19B2 of Spring-8. The resulting SAXS data were subjected to fitting by Guinier approximation using a spherical model to determine the average particle size $D_c$ of the catalytic material. For example, the average particle size of metal fine particles was determined with respect to each of the catalyst structures of Examples 6 to 8, which contains, as a catalytic material, metal fine particles including Fe and Zr as the first and second elements, respectively. For comparison, commercially available Fe fine particles (manufactured by Wako) were observed and measured using SEM. Table 2 shows the results.

The results were as follows. In the commercially available product, Fe fine particles were found at random with different particle sizes in the range of 50 nm to 400 nm. On the other hand, as a result of SAXS measurement, a sharp scattering peak, which indicates a uniform particle size, was detected for the particle size shown in Table 2 from the catalyst structure of each of the examples, in which the functional material has an average particle size of 1.5 nm to 1.6 nm. The results of SAXS measurement and SEM/EDX cross-sectional measurement revealed that metal fine particles (Fe fine particles) with particle sizes of 10 nm or less for serving as a functional material were uniform in particle size and extremely highly dispersed in enlarged pore portions inside the support.

SEM/EDX and SAXS analyses were also performed on the catalyst structures of the other examples. As a result, metal fine particles including the first element shown in Table 2 were found to exist in each of the catalyst structures. The catalyst structure of each of the examples was subjected to trace metal element analysis using inductively coupled plasma (ICP). As a result, the second element shown in Table 2 was found to exist in the metal fine particles. Therefore, it has been found that, in each of the catalyst structures, fine metal particles including one or both of the first and second elements were held as a functional material or materials in zeolite. It has also been found that, in the catalyst structure, the functional material is in the form of fine particles including the first and second elements or in the form of fine particles including the first or second element alone.

(C) Relationship Between the Amount of First and Second Elements Added to Precursor Material (A) and the Content of First and Second Elements Enclosed Inside Support in Catalyst Structure Catalyst structures each composed of a support and metal fine particles as a functional material enclosed inside the support were prepared using the precursor material (A) impregnated with the metal-containing solution in which the precursor material (A) had a $Si/M_1$ atomic ratio of 100 and a $Si/M_2$ atomic ratio of 2,000, wherein $M_1$ is the content of the first element (cobalt (Co), iron (Fe), nickel (Ni), or ruthenium (Ru)) in the precursor material (A), and $M_2$ is the content of the second element (Zr) in the precursor material (A). Subsequently, each of the catalyst structures prepared with the contents shown above was measured for the content (% by mass) of metal enclosed inside the support.

The metal content was determined using ICP (inductively coupled plasma) alone or a combination of ICP and X-ray fluorescence (XRF) analysis. XRF analysis (using energy dispersive X-ray fluorescence analyzer SEA1200VX manufactured by SII Nanotechnology Inc.) was carried out in a vacuum atmosphere under conditions at an acceleration voltage of 15 kV (using a Cr filter) or an acceleration voltage of 50 kV (using a Pb filter). In XRF analysis method, the abundance of metals is determined from fluorescence intensity, and the metals cannot be quantified (in units of % by mass) by XRF analysis alone. Therefore, ICP analysis was used to quantify the content of metals in the catalyst structure containing metals in such amounts that the $Si/M_1$ atomic ratio and the $Si/M_2$ atomic ratio were 100 and 2,000, respectively.

(D) Performance Evaluation

The catalyst structures of the examples and the silicalites of the comparative examples were evaluated for the catalytic ability of the functional material. Table 2 shows the results.

(1) Catalytic Activity

As an example, catalytic activity for FT synthesis reaction was evaluated under the conditions shown below. First, an atmospheric pressure flow reactor was filled with 70 mg of the catalyst structure. While hydrogen (8 mL/min) and carbon monoxide (4 mL/min) were supplied to the reactor and the pressure in the reactor was adjusted to 0.1 MPa, the temperature in the reactor was raised at 20° C./min in the temperature range of 100 to 700° C. and then held for 1 hour for Fischer-Tropsch synthesis reaction of hydrogen and carbon monoxide. The atmospheric pressure flow reactor used was a single microreactor (Rx-3050SR available from Frontier Laboratory).

After the completion of the reaction, the collected gas and liquid products were subjected to componential analysis using gas chromatography-mass spectrometry (GC/MS). The gas and liquid products were analyzed using an analyzer TRACE 1310GC (manufactured by Thermo Fisher Scientific Inc., detector: thermal conductivity detector).

Based on the results of the analysis, the rate of conversion of the substrate gas (carbon monoxide) to hydrocarbons at 250° C. was calculated. A substrate gas conversion rate of 9% or more was evaluated as good catalytic activity (o), and a substrate gas conversion rate of less than 9% was evaluated as poor (unacceptable) catalytic activity (x).

(2) Durability (Life)

The durability was evaluated under the conditions shown below. First, the catalyst structure used in the evaluation (1) was recovered and then heated at 650° C. for 12 hours. After the heating, the catalyst structure was subjected again to the FT synthesis reaction using the same method as in the evaluation (1). The resulting gas and liquid products were subjected to componential analysis using the same method as in the evaluation (1).

Based on the results of the analysis, the amount of the produced hydrocarbons was determined using the same method as in the evaluation (1). A comparison in the amount of the produced hydrocarbons was also made between before and after the heating of the catalyst structure to determine what extent the yield of hydrocarbons with the catalyst structure was retained after the heating. Specifically calculated was the percentage (%) of the amount of hydrocarbons produced with the catalyst structure after the heating (the amount of production determined in the evaluation (2)) to the amount of hydrocarbons produced with the catalyst structure before the heating (the amount of production determined in the evaluation (1)).

With respect to each of the examples, calculated was the ratio of the amount of hydrocarbons produced with the catalyst structure after the heating (the amount of production determined in the evaluation (2)) to the amount of hydrocarbons produced with the catalyst structure before the heating (the amount of production determined in the evaluation (1)). Cases where the ratio was maintained at 60% or more were evaluated as high durability (heat resistance) (o), and cases where the ratio was reduced to less than 60% were evaluated as low (unacceptable) durability (heat resistance) (x).

The samples of Comparative Examples 1 to 2 were also evaluated for performance in the same manner as in the evaluations (1) and (2). It should be noted that the sample of Comparative Example 2 is a support itself with no functional material. For the performance evaluation, therefore, the reactor was filled only with the support of Comparative Example 2 instead of the catalyst structure. The results are shown in Tables 1 and 2.

TABLE 1

Conditions for production of catalyst structure

| No. | Precursor material (A) Type | Precursor material (A) Pore size (nm) | Addition to precursor material (A) Calculated ratio (atomic ratio) for the amount of added first element $Si/M_1$ | Addition to precursor material (A) Ratio (atomic ratio) for the amount of added second element $Si/M_2$ | Conditions for hydrothermal treatment using precursor material (C) Type of structure-directing agent | Conditions for hydrothermal treatment using precursor material (C) pH | Conditions for hydrothermal treatment using precursor material (C) Time (h) |
|---|---|---|---|---|---|---|---|
| Example 1 | MCM-41 | 2 | 50 | 1000 | TPABr | 12 | 72 |
| Example 2 | | 2 | 100 | 2000 | TPABr | | 72 |
| Example 3 | | 2 | | 2000 | Absent | | 96 |
| Example 4 | | 2 | | 2000 | TEAOH | | 144 |
| Example 5 | MCM-41 | 2 | 100 | 2000 | TPABr | 12 | 72 |
| Example 6 | MCM-41 | 2 | 100 | 2000 | TPABr | 12 | 72 |
| Example 7 | | 2 | | 2000 | Absent | | 96 |
| Example 8 | | 2 | | 2000 | TEAOH | | 144 |
| Example 9 | MCM-41 | 2 | 100 | 2000 | TPABr | 12 | 72 |
| Example 10 | | 2 | | 2000 | Absent | | 96 |
| Example 11 | | 2 | | 2000 | TEAOH | | 144 |
| Example 12 | MCM-41 | 2 | 100 | 2000 | TPABr | 12 | 72 |
| Example 13 | | 2 | | 2000 | Absent | | 96 |
| Example 14 | | 2 | | 2000 | TEAOH | | 144 |
| Comparative Example 1 | | | | — | | | |
| Comparative Example 2 | | | | — | | | |

TABLE 2

Catalyst structure

| No. | Support Zeolite-type compound Structure | Support Zeolite-type compound Average inner diameter of all channels $D_F$ [nm] | Functional material Metal fine particles First element | Functional material Metal fine particles Second element | Functional material Metal fine particles Average particle size $D_C$ [nm] | $D_C/D_F$ | Content of first element in catalyst structure (A) [mass %] | Content of second element in catalyst structure (B) [mass %] | Ratio of second element amount to first element amount (B/A) | Performance evaluation Catalytic activity | Performance evaluation Durability |
|---|---|---|---|---|---|---|---|---|---|---|---|
| Example 1 | MFI | 0.54 | Co | Zr | 1.6 | 3 | 2 | 0.1 | 0.05 | ○ | ○ |
| Example 2 | MFI | 0.54 | Co | Zr | 1.6 | 3 | 0.64 | 0.036 | 0.06 | ○ | ○ |
| Example 3 | MOR | 0.6 | | | 1.6 | 2.7 | 0.64 | 0.036 | 0.06 | ○ | ○ |
| Example 4 | BEA | 0.67 | | | 1.6 | 2.4 | 0.64 | 0.036 | 0.06 | ○ | ○ |
| Example 5 | MFI | 0.54 | Co | Zr | 1.6 | 3 | 0.64 | 0.036 | 0.06 | ○ | ○ |
| Example 6 | MFI | 0.54 | Fe | Zr | 1.6 | 3 | 0.6 | 0.036 | 0.06 | ○ | ○ |
| Example 7 | MOR | 0.6 | | | 1.6 | 2.7 | 0.6 | 0.036 | 0.06 | ○ | ○ |
| Example 8 | BEA | 0.67 | | | 1.6 | 2.4 | 0.6 | 0.036 | 0.06 | ○ | ○ |
| Example 9 | MFI | 0.54 | Mi | Zr | 1.6 | 3 | 0.64 | 0.036 | 0.06 | ○ | ○ |
| Example 10 | MOR | 0.6 | | | 1.6 | 2.7 | 0.64 | 0.036 | 0.06 | ○ | ○ |
| Example 11 | BEA | 0.67 | | | 1.6 | 2.4 | 0.64 | 0.036 | 0.06 | ○ | ○ |
| Example 12 | MFI | 0.54 | Ru | Zr | 1.5 | 2.8 | 1.09 | 0.036 | 0.03 | ○ | ○ |
| Example 13 | MOR | 0.6 | | | 1.5 | 2.5 | 1.09 | 0.036 | 0.03 | ○ | ○ |
| Example 14 | BEA | 0.67 | | | 1.5 | 2.2 | 1.09 | 0.036 | 0.03 | ○ | ○ |
| Comparative Example 1 | MFI | 0.54 | Co | Zr | 1.6 | 3 | 0.64[X.1] | 0.036 | 0.06 | x | x |
| Comparative Example 2 | MFI | 0.54 | — | — | — | — | — | — | — | x | x |

[X.1]indicting the content of each of the first and second elements in metal fine particles deposited on the outer surface of the support.

Tables 1 and 2 show that the catalyst structures (Examples 1 to 14), found to hold metal fine particles as a functional material inside the support in the cross-sectional observation, have higher catalytic activity and higher durability than the catalyst structure (Comparative Example 1) having metal fine particles including the first and second elements as a functional material only deposited on the outer surface of the support or than the support itself (Comparative Example 2) with no functional material.

The catalyst structures subjected to the evaluation (C) were also evaluated for the relationship between the content (% by mass) of metal enclosed inside the support and the catalytic activity determined in the evaluation (1). The evaluation was performed using the same method as in the performance evaluation (D) for (1) catalytic activity. As a result, it has been found that the catalytic activity tends to increase when the calculated $Si/M_1$ atomic ratio for the amount of the first element added to the precursor material (A) is 50 to 100 and the calculated $Si/M_2$ atomic ratio for the amount of the second element added to the precursor material (A) is 1,000 to 2,000 (when the content of the first element ($M_1$) in the catalyst structure is 0.60 to 2.00% by mass and the content of the second element ($M_2$) in the catalyst structure is 0.036 to 0.100% by mass).

Separately, the catalyst structures according to the present invention were evaluated for the relationship between the content (% by mass) of metal enclosed inside the support and the catalytic activity determined in the evaluation (1). The evaluation was performed using the same method as in the performance evaluation (D) for (1) catalytic activity. As a result, it has been found that the catalytic activity tends to increase when the calculated $Si/M_1$ atomic ratio for the amount of the first element added to the precursor material (A) is 10 to 1,000 and more preferably 30 to 300 (when the total content of the first element ($M_1$) of the functional material in the catalyst structure is 0.5 to 7.6% by mass and more preferably 0.5 to 2.5% by mass).

On the other hand, the catalyst structure of Comparative Example 1 having cobalt (Co) and zirconium (Zr) as functional materials only deposited on the outer surface of the support and the support of Comparative Example 2 with no functional material present have lower catalytic activity and lower durability than the catalyst structures of Examples 1 to 14.

The results shown above suggest that the catalyst structures (Examples 1 to 14) have excellent catalytic activity and excellent durability.

Other Embodiments

A method of using a catalyst structure is provided including using a catalyst structure including: a support that has a porous structure and includes a zeolite-type compound; and at least one functional material present in the support, wherein the functional material includes at least one first metal element selected from the group consisting of cobalt (Co), nickel (Ni), iron (Fe), and ruthenium (Ru); and at least one second metal element selected from the group consisting of metal elements belonging to Groups 1, 2, 4, 7, and 12 of the periodic table, the support has channels communicating with one another, and the functional material is present at least in an enlarged pore portion of the channel of the support.

EXPLANATION OF REFERENCE NUMERALS

1: catalyst structure
10: Support
10a: Outer surface
11: Channel
11a: Pore
12: enlarged pore portion
20: Functional material
30: Functional material
$D_C$: Average particle size
$D_F$: Average inner diameter
$D_E$: Inner diameter

The invention claimed is:

1. A catalyst structure comprising:
a support that has a porous structure and comprises a zeolite-type compound; and
a functional material present in the support,
the functional material comprising:
a first metal element selected from the group consisting of cobalt (Co), nickel (Ni), iron (Fe), and ruthenium (Ru); and
a second metal element selected from the group consisting of metal elements belonging to Groups 1, 2, 4, 7, and 12 of periodic table, wherein
the support has channels communicating with one another,
the functional material is present at least in the channels of the support,
the channels have any one of a one-dimensional pore a two-dimensional pore, a three-dimensional pore of a framework structure of the zeolite-type compound, and an enlarged pore portion which is not defined by the framework structure of the zeolite-type compound and has a diameter greater than any one of the one-dimensional pore, the two-dimensional pore and the three-dimensional pore,
the enlarged pore portion has a greater diameter than the functional material,
the functional material has a diameter greater than any one of the one-dimensional pore, the two-dimensional pore and the three-dimensional pore,
the functional material includes metal oxide nanoparticles, and
the framework structure of the zeolite-type compound is selected from the group consisting of FAU type, MTW type, MFI type, FER type, LTA type, MWW type, MOR type, LTL type, and BEA type.

2. The catalyst structure according to claim 1, wherein the second element is at least one metal element selected from the group consisting of potassium (K), magnesium (Mg), titanium (Ti), zirconium (Zr), manganese (Mn), and zinc (Zn).

3. The catalyst structure according to claim 1, wherein a mass ratio of a content of the second element to a content of the first element is from 0.01 to 2.00.

4. The catalyst structure according to claim 1, wherein a total content of the first element is 0.5% by mass or more with respect to the mass of the catalyst structure.

5. The catalyst structure according to claim 1, wherein a total content of the second element is 5% by mass or less with respect to the mass of the catalyst structure.

6. The catalyst structure according to claim 1, wherein a content of the second element is lower than a content of the first element.

7. The catalyst structure according to claim 1, wherein the functional material is in the form of metal oxide particles comprising one or both of an oxide of the first element and an oxide of the second element.

8. The catalyst structure according to claim 1, wherein the functional material is in the form of metal particles comprising one or both of the first element and the second element.

9. The catalyst structure according to claim 8, wherein the metal particles comprise one or both of: particles of an alloy comprising the first element and the second element; and at least two types of single metal particles comprising particles of the first element and particles of the second element.

10. The catalyst structure according to claim 1, wherein;
the enlarged pore portion is different from all of the one-, two-, and three-dimensional pores, and
the functional material is present at least in the enlarged pore portion.

11. The catalyst structure according to claim 10, wherein the enlarged pore portion connects a plurality of pores constituting one of the one-, two-, and three-dimensional pores.

12. The catalyst structure according to claim 10, wherein the functional material has an average particle size equal to or smaller than an inner diameter of the enlarged pore portion.

13. The catalyst structure according to claim 10, wherein the enlarged pore portion has an inner diameter of 0.5 nm to 50 nm.

14. The catalyst structure according to claim 1, wherein the functional material has an average particle size larger than an average inner diameter of the channels.

15. The catalyst structure according to claim 1, wherein the functional material has an average particle size of 0.08 nm to 30 nm.

16. The catalyst structure according to claim 1, wherein a ratio of an average particle size of the functional material to an average inner diameter of the channels is from 0.05 to 300.

17. The catalyst structure according to claim 1, wherein the channels have an average inner diameter of 0.1 nm to 1.5 nm.

18. The catalyst structure according to claim 1, further comprising at least one additional functional material held on an outer surface of the support.

19. The catalyst structure according to claim 18, wherein the additional functional material comprises one or more metals selected from the group consisting of cobalt (Co), nickel (Ni), iron (Fe), ruthenium (Ru), and an alloy thereof.

20. The catalyst structure according to claim 18, wherein the additional functional material comprises one or more metals selected from the group consisting of elements belonging to Groups 1, 2, 4, 7, and 12 of periodic table, and an alloy thereof.

* * * * *